United States Patent [19]

Evers

[11] 4,055,578
[45] * Oct. 25, 1977

[54] CERTAIN FURAN-3-THIOLS, CERTAIN DIHYDRO DERIVATIVES THEREOF AND 2,5-DIMETHYLTETRAHYDROFURAN-3-THIOL

[75] Inventor: William John Evers, Red Bank, N.J.

[73] Assignee: International Flavors & Fragrances Inc., New York, N.Y.

[*] Notice: The portion of the term of this patent subsequent to Apr. 26, 1994, has been disclaimed.

[21] Appl. No.: 605,393

[22] Filed: Aug. 18, 1975

Related U.S. Application Data

[60] Division of Ser. No. 295,859, Oct. 10, 1972, which is a continuation of Ser. No. 864,227, Oct. 6, 1969, abandoned, which is a continuation-in-part of Ser. No. 796,923, Feb. 5, 1969, Pat. No. 3,666,495.

[51] Int. Cl.$^2$ .................. C07D 307/64; C07D 307/38
[52] U.S. Cl. ............................................. 260/347.2
[58] Field of Search ...................................... 260/347.2

[56] References Cited

U.S. PATENT DOCUMENTS 3,394,016  7/1968  Bidmead et al. ..................... 426/250

FOREIGN PATENT DOCUMENTS 946,441  2/1956  Germany

Primary Examiner—Henry R. Jiles
Assistant Examiner—Bernard Dentz
Attorney, Agent, or Firm—Brooks, Haidt, Haffner & Delahunty

[57] ABSTRACT

Novel furanthiols of the formula

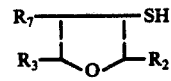

wherein $R_2$, $R_3$ and $R_7$ is hydrogen or alkyl and the dashed lines represent single or double carbon-to-carbon bonds are prepared and isolated.

10 Claims, No Drawings

CERTAIN FURAN-3-THIOLS, CERTAIN DIHYDRO DERIVATIVES THEREOF AND 2,5-DIMETHYLTETRAHYDROFURAN-3-THIOL

This application is a division of my application Ser. No. 295,859 filed on Oct. 10, 1972 which in turn is a continuation of application Ser. No. 864,227 filed Oct. 6, 1969, now abandoned, which is a continuation-in-part of application Ser. No. 796,923 filed Feb. 5, 1969, now U.S. Pat. No. 3,666,495 issued May 30, 1972.

Artificial flavoring agents for foodstuffs have received increasing attention in recent years. In many areas, such food flavoring agents are preferred over natural flavoring agents, at least in part because of the uniform flavor that may be so obtained. For example, natural food flavoring agents such as extracts, essences, concentrates and the like are often subject to wide variation due to changes in the quality, type, and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned goods, sauces, gravies, and the like are apt to be stored by the consumer for some time prior to use.

The fundamental problem in preparing artificial flavoring agents is that of achieving as nearly as possible a true flavor reproduction. This generally proves to be a difficult task since the mechanism for flavor development in many foods is not understood. This is notable in products having meaty and roasted flavor characteristics.

Reproduction of roasted and meat flavors and aromas has been the subject of a long and continuing search by those engaged in the production of foodstuffs. The severe shortage of foods, especially protein foods, in many parts of the world has given rise to the need for utilizing non-meat sources of proteins and making such proteins as palatable and as meat-like as possible. Hence, materials which will closely simulate or exactly reproduce the flavor and aroma of roasted products and meat products are required.

Moreover, there are a great many meat-containing or meat-based foods presently distributed in a preserved form, examples being condensed soups, dry soup mixes, dried meat, freeze-dried or lyophilized meats, packaged gravies, and the like. While these products contain meat or meat extracts, the fragrance, taste, and other organoleptic factors are very often impaired by the processing operations, and it is desirable to supplement or enhance the flavors of these preserved meat foods.

THE INVENTION

The present invention provides novel materials having desirable meat, roast meat, and roasted fragrance and flavor notes. These materials are organic oxygen-containing heterocyclics wherein the second carbon atom from the oxygen atom contains a sulfur substituent. Such materials include furan derivatives having the formula:

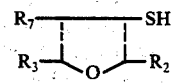

wherein $R_2$, $R_3$ and $R_7$ are hydrogen or alkyl and the dashed lines represent single or double carbon-to-carbon bonds.

The present invention also contemplates flavoring and flavor-enhancing compositions containing the 3-sulfur substituted furan derivatives, and foodstuffs and food compositions containing such furan derivatives. The methods for preparing such furan derivatives and such food compositions are also contemplated within the present disclosure.

When $R_2$, $R_3$, and $R_7$ represent alkyl groups, it is desirable that they be lower alkyl groups having up to five carbon atoms. Thus, for example, these groups can be methyl, ethyl, propyl, isopropyl, butyl, secondary butyl, pentyl.

It has been found that when both dashed lines represent double bonds, that is, when the ring is a furyl ring, the compounds have a desirable pronounced meat flavor and aroma characteristic. When the furan ring is more highly saturated, and particularly when the ring is dihydrofuryl, a roasted flavor and aroma characteristic is more dominant.

The novel compounds of the present invention are oily liquids or crystalline solids and are, in general, characterized by pronounced pleasant roasted food flavor and aroma at the levels taught herein. The dominant note is one of roasted protein with a notable absence of any pungency or lachrymose factor.

It will be understood that some of the novel compounds of this invention can exist in various isomeric forms, and the formulas given herein include such isomers. By way of example, the 2-methyl-[2,3H]-dihydrofuran-3-thiols exist as geometric isomers and as optical isomers. A representation of one of the isomers of this compound is as follows:

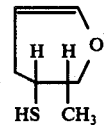

Another isomer is:

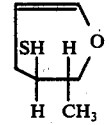

Exemplary of 3-sulfur substituted furans contemplated herein are:
2-methyldihydrofuran-3-thiol
2-methyltetrahydrofuran-3-thiol
2-ethyldihydrofuran-3-thiol
2-ethyltetrahydrofuran-3-thiol
2-isopropyldihydrofuran-3-thiol
2-isopropyltetrahydrofuran-3-thiol
2-propyldihydrofuran-3-thiol
2,5-dimethyldihydrofuran-3-thiol
2,5-dimethyltetrahydrofuran-3-thiol
2,5-diethyldihydrofuran-3-thiol
2,5-diethyltetrahydrofuran-3-thiol
2-ethyl-5-methyldihydrofuran-3-thiol
2-ethyl-5-methyltetrahydrofuran-3-thiol
2-ethyl-5-propyltetrahydrofuran-3-thiol
2-methylfuran-3-thiol
2-propylfuran-3-thiol
2-isopropylfuran-3-thiol 2,5-dimethylfuran-3-thiol
2-ethyl-5-methylfuran-3-thiol
2-methyl-5-ethylfuran-3-thiol
2,5-dipropylfuran-3-thiol
2,5-diisopropylfuran-3-thiol
5-isopropyl-2-methylfuran-3-thiol
2-butylfuran-3-thiol It will be understood from the present disclosure that the derivatives of dihydrofuran can be 2,3H or 4,5H. Thus, 2-methyldihydrofuran-3-thiol includes 2-methyl-[4,5H]-dihydrofuran-3-thiol and 2-methyl-[2,3H]dihydrofuran-3-thiol.

In accordance with a further aspect of this invention, the novel sulfur compounds are utilized singly, in admixture, or in combination with other edible materials to impart a meaty or roasted organoleptic impression to foods or edible materials. Thus, the compounds herein described can comprise flavoring compositions and flavor-enhancing compositions. It will be understood herein that a flavoring composition is one capable of imparting a definite flavor to a tasteless or bland foodstuff, and a flavor-enhancing composition is one capable of reinforcing one or more flavor notes of a natural or other material which is deficient in flavor. A flavor-enhancing composition would be useful for improving the flavor of, say, a canned meat product, the flavor of which was diminished or undesirably altered by the processing. It will accordingly be understood that the disclosed sulfur-containing compounds can be mixed with other flavoring ingredients, carriers, vehicles and the like to form compositions suitable for imparting a flavor to, enhancing the flavor in, or altering the flavor of, a food composition, and such food compositions and the methods for preparing them are included in this disclosure. The furyl monosulfides, disulfides, and mercaptans of this invention generally impart a meat or cooked meat flavor and aroma. The dihydrofuryl sulfides, disulfides, and mercaptans impart a roasted flavor and odor which is even redolent of roasted sesame seeds in some instances. Their flavor characteristics are sufficiently pronounced and persistent that a desirable flavor and odor can be developed by simply using the undiluted compound or compounds; for example, by addition of the undiluted compound to a processed fish meal.

When the sulfur compounds of this invention are used in flavoring compositions to enhance existing flavors in, or to provide the entire flavor impression to, a foodstuff, they can be combined with organic acids including fatty, saturated, unsaturated and amino acids, alcohols, including primary and secondary alcohols, esters, carbonyl compounds including aldehydes and ketones, lactones, cyclic organic materials including benzene derivatives, alicyclics, heterocyclics such as furans, pyridines, pyrazines and the like, sulfur-containing materials including thiols, sulfides, disulfides and the like, proteins, lipids, carbohydrates, and so-called flavor potentiators such as monosodium glutamate, guanylates, inosinates, natural flavoring materials such as vanillin, and the like. It will be appreciated that the types and amounts of materials selected from the foregoing groups of materials will depend upon the precise organoleptic character desired in the finished product and, especially in the case of flavoring compositions used to enhance other flavors, will vary according to the foodstuff to which the flavor and aroma are to be imparted. Inorganic materials such as sodium chloride and freshness preservers such as butylated hydroxyanisole, butylated hydroxytoluene and propyl gallate can be added for their adjuvant or preservative effects on the flavoring composition or on the final food composition itself.

As noted above, it can also be desirable to utilize carriers such as gum arabic and carrageenen or vehicles such as ethyl alcohol, water, propylene glycol. When the carrier is an emulsion, the flavoring composition can also contain emulsifiers such as mono- and diglycerides of fatty acids and the like. With these carriers or vehicles the desired physical form of the composition can be prepared. It will be understood that the compounds of this invention can be used in spray-dried, liquid, encapsulated, emulsified and other forms in which flavorings are added to foodstuffs. The compounds can be so used alone or in combination with the other ingredients set forth therein. In the case of a foodstuff which is prepared from a combination of ingredients the furyl sulfur derivatives, flavor enhancers and flavoring compositions of this invention can be added to one of the ingredients and thereby be incorporated into the composition as a whole.

The amount of novel sulfur-containing compound or compounds used should be sufficient to impart a meaty or roasted flavor and aroma note to the ultimate foodstuff in which they are used. Thus, a small but effective amount of 3-sulfur substituted furan sufficient to provide the meaty flavor note in, or to round out the meat, roasted, or other flavor note in, the ultimate foodstuff is used. The amount will vary depending upon the ultimate food composition to be flavored; for example, more may be required in producing a full, rounded meat flavor in an unflavored material and less may be required when this invention is used to enhance a meat or roasted foodstuff or flavoring material which is deficient in natural flavor or aroma.

Those skilled in the art will appreciate that the amount of furyl sulfur derivatives according to this invention can be varied over a range to provide the desired flavor and aroma. The use of too little of the derivative of derivatives will not give the full benefit, while too much will make the flavor compositions and foodstuffs needlessly costly, and in extreme cases will unbalance the flavor and aroma so that optimum results are not obtained.

It is accordingly preferred that the ultimate food composition contain at least about 1.0 part per billion of the sulfur derivatives, based on total composition, and it is not generally desirable to use more than about 500 parts per million (ppm) in the finished composition. Thus, the desirable range for use in the practice of this invention is from about 0.001 to about 500 ppm of the furyl sulfur compound or compounds. When these compounds are added to the foodstuff in the form of a meat flavor composition, the amount should be sufficient to impart the requisite flavor and/or aroma note to the composition so that the flavor and aroma will be balanced in the finished foodstuff. Accordingly, the flavoring compositions of this invention preferably contain from about 0.0001 to 10% of sulfur derivatives based on the total weight of said flavoring composition. Unless otherwise indicated, all parts, proportions, percentages, and ratios herein are by weight.

The flavoring compositions of this invention can be added to the foodstuffs by conventional methods known in the art. The flavor material of this invention, together with any other liquids if desired, can be admixed with a carrier, such as gum arabic, gum tragacanth, carrageenen and the like, and spray-dried to obtain a particulate solid flavoring material. Where a powdered prepared flavor mix is being made, the dried solids and flavoring compositions or furyl sulfur derivatives of this invention are mixed together in a dry blender to attain uniformity.

When liquid materials are involved in the preparation of foodstuffs, the flavoring materials of this invention can be combined with either the liquid to be used in the finished composition, or alternatively they can be added with a liquid carrier in which they are dissolved, emulsified, or otherwise dispersed.

It has also been discovered than furan-3-thiols and alkyl-substituted furan-3-thiols can be produced by the reaction of an appropriate dihydrofuranone-3 or tetrahydrofuranone-3 with hydrogen sulfide in the presence of anhydrous hydrogen chloride at temperature of $-60°$ to $-100°$ C. This reaction provides furan-3-thiols; dihydrofuran-3-thiols; and tetrahydrofuran-3-thiones, as well as alkyl-substituted derivatives thereof.

The reaction of the di- or tetrahydrofuranone-3 or alkylated counterparts with hydrogen sulfide in the presence of gaseous hydrogen chloride will take place in from about 5 up to about 25 hours at temperatures of about $-60°$ down to about $-100°$ C. The reaction vehicle can be any polar solvent having a melting point below about $-100°$ C. and a viscosity such that the reaction mass can be turbulently mixed at that temperature. Desirable polar solvents having the above properties are Diglyme, tetrahydrofuran, methonal, ethanol and the like. The hydrogen sulfide reactant is preferably in about a 5- to 10-fold excess over the furanone-3.

It will be understood that the thione can readily be converted to the corresponding thiol with a reducing agent such as lithium aluminum hydride, diethoxy aluminum hydride, ethoxy aluminum dihydride and the like. The vehicle for this reduction can be an oxygenated solvent such as diethyl ether, tetrahydrofuran, Diglyme (dimethyl ether of diethylene glycol), and the like. The temperature of the reaction can vary from about 0° C. up to the reflux temperature of the reaction medium. Although the reaction can be carried out over a range of pressures, it is preferred that the pressure be atmospheric. The reducing agent is preferably in excess molar proportion relative to the thione.

It will be understood that the corresponding bis(3-furyl), bis(3-dihydrofuryl), and bis(3-tetrahydrofuryl) disulfides can be produced by oxidizing the corresponding thiols under mild oxidizing conditions. Thus, the thiols can be oxidized with an air stream bubbled through them at 20° C. and 760 mm. Hg pressure for 8 hours. Stirring of the reaction mass with use of baffles during the bubbling is adequate to maintain suitable contact between the reactants. Other suitable mild oxidizing agents include ferric chloride, iodine-potassium iodide, dimethyl disulfide, dimethylsulfoxide and the like.

The time of this mild oxidation reaction will vary from substantially instantaneous up to 20 hours at temperatures from about 10° to 50° C. and atmospheric pressure. The pH of the reaction mass depends upon the nature of the oxidizing agent; as does the time of reaction which is a function of the net oxidation reduction potential of the reactants and the concentrations and relative proportions of the reactants. It is preferred that stoichiometric quantities of thiol and oxidizing materials be used unless such easy-to-remove oxidizing agents as dimethyl sulfoxide, dimethyl sulfide and the like are employed, in which case an excess of such oxidizing agents be utilized.

In another process contemplated herein a 2-alkyl-5-furoic acid, 2-alkyl-5-cyanofuran, or a 2-alkyl-5-halofuran is treated with oleum (fuming sulfuric acid) to produce the 3-sulfo derivative. When the 5-furoic acid is used, the barium salts of the resulting acid are then obtained by treatment of the acid with barium carbonate which is used in excess so as to eliminate any unreacted sulfuric acid. The barium salt is converted to the sodium salt which is then decarboxylated with an equivalent amount or an excess of mercuric chloride in a refluxing aqueous solution. The resulting sodium sulfonate is reacted with a 7-8 fold excess of thionyl chloride, the excess of thionyl chloride being used as a solvent in the presence of a trace of dimethyl formamide. In place of excess thionyl chloride, other inert solvents may be used, for example, benzene, hexane or diethyl ether. The resulting 3-chlorosulfo group is reduced to the thiol (—SH) group by reaction with a reducing agent used in excess to insure total reduction. Agents such as lithium aluminum hydride, mono-alkoxy aluminum dihydride, dialkoxy aluminum hydride or zinc in hydrochloric acid wherein each of these reducing agents is in a vehicle can be used. Such a reduction can be carried out at room temperature to reflux under atmospheric pressure. The vehicle carring the reducing agent can be oxygenated vehicles such as diethyl ether, tetrahydrofuran, Diglyme, and the like.

Saturated furan-3-thiols can also be produced by treating alkyl-3-halotetrahydrofurans with sodium hydrosulfide under reflux conditions in the presence of ethanol, methanol, or like vehicles. The mercaptans of this invention can, if desired, be reacted with various chlorosulfur compounds to obtain di- or tri- or tetrasulfides. Thus, a thiol such as 2-methyl-3-furan thiol can be reacted with an equimolar amount of methyl disulfur chloride, $CH_3S_2Cl$, at a temperature of from $-60°$ C. up to about 0° C. to produce methyl(2-methyl-3-furyl) trisulfide. This reaction can be carried out in a solvent such as diethyl ether, cyclohexane, hexane, carbon tetrachloride, benzene and the like. Similarly, a thiol such as 2-methyl-3-furanthiol can be reacted with an equimolar amount of methanesulfenyl chloride, $CH_3SCl$, to produce methyl (2-methyl-3-furyl) disulfide. This reaction also can be carried out in a solvent such as diethyl ether, cyclohexane, hexane carbon tetrachloride, benzene and the like. The reaction temperature is preferably from $-60°$ C. up to 0° C. at atmospheric pressure.

The di- and tetrahydro materials according to this invention are also conveniently prepared directly from the appropriate alkyl or dialkyl di- or tetrahydrofurans, under reaction conditions similar to the conditions used in the analogous reactions described heretofore.

The bis(2-methyl-3-furyl) disulfide and 2-methyl-3-furan thiol of this invention can also be obtained by: (a) forming a mixture of thiamine, cysteine, hydrolyzed vegetable protein and water and heating the mixture to reflux for a period of from about 2 to about 10 hours as shown in U.S. Pat. No. 3,394,016; (b) removing the distillate at intervals; (c) treating the distillate in an extractive process using as an extractant a low boiling solvent such as methylene chloride and the like, whereby the bis(2-methyl-3-furyl) disulfide and 2-methyl-3-furan thiol of this invention are obtained; (d) separating the furyl sulfur compounds from the mixture by means of, for example, a gas-liquid chromatographic column or column chromatographic techniques.

The following examples are given to illustrate embodiments of the invention as it is presently preferred to practice it. It will be understood that these examples are illustrative, and the invention is not to be considered as restricted thereto except as indicated in the appended claims.

EXAMPLE I

Production of furan-3-thiol derivatives

A 250 ml. flask fitted with a mechanical stirrer, gas inlet tube, calcium chloride drying tube, thermometer, and Y-tube is charged with 50 ml. of distilled diglyme, and the diglyme is saturated with gaseous hydrogen chloride at 0°–5° C. with constant stirring.

The flask is then immersed in a Dry Ice-isopropanol bath at −80° C. The cooled flask is charged with 14.0 g (0.14 mole) of 2-methyl-3-tetrahydrofuranone, and 28.5 g. (0.84 mole) of hydrogen sulfide which has been chilled to −80° C. is slowly warmed and allowed to boil over into the reaction flask.

About one-half hour after the beginning of the hydrogen sulfide addition a pink-red color begins to appear in the reaction mixture. By the end of the 2.5 hours required for the addition of all the hydrogen sulfide, the reaction mixture is orange in color. At this time stirring is stopped, and the reaction mixture is permitted to stand 16 hours.

A 1-liter Erlenmeyer flask is charged with sufficient sodium bicarbonate to cover the bottom of the flask and is placed into a Dry Ice-isopropanol bath. The reaction mixture is then poured slowly over the sodium bicarbonate to minimize foaming. Additional sodium bicarbonate is added until all foaming ceases. The neutralized mixture is treated with 200 ml. of water and quickly extracted with 100 ml. of methylene chloride. The organic solution so obtained is dried and concentrated to provide 39.5 grams of an oil. The oil is distilled under vacuum to provide a first cut taken at 73°–80° C. at 57 mm.Hg and a second cut at 8°–83° C. at the same pressure.

The 25 ml. of the second portion is dissolved in 100 ml. of ethyl ether and extracted four times with 5 ml. of 5% aqueous sodium hydroxide to remove the pink color. The basis fraction so obtained is acidified with 11.2 cc of hydrochloric acid and extracted twice with 10 ml. of ethyl ether, dried over sodium sulfate, and concentrated.

This concentrate is then chromatographed to separate the 2-methylfuran-3-thiol and 2-methyl-[4,5H]-dihydrofuran-3-thiol produced. These thiols have a roast meat aroma.

The analytical data on the 2-methylfuran-3-thiol are:

| | Infra-red |
|---|---|
| $\lambda_{max.}$ | Interpretation |
| 3.92 | S-H group conjugated with aromatic ring. |
| 7.40, 6.60 | Aromatic ring C=C bond. |
| 7.26 | Methyl group. |
| 13.58 | C—H bond of aromatic ring. |

Proton magnetic resonance.
In carbon tetrachloride:
2.12 (doublet, 3 protons),
2.23 (doublet, 1 proton),
6.08 (doublet, 1 proton), and -continued Proton magnetic resonance.
In carbon tetrachloride:
7.04 p.p.m. (doublet, 1 proton).

Mass spectrum

Base peak 43, molecular peak 114. Other peaks in descending order 41, 45, 85, 47, 113, 71, 75, 74.

EXAMPLE II

Preparation of bis(2-methyl-3-furyl)disulfide.

The thiol produced in Example I is oxidized under mild conditions by dissolving 5 g. of the thiol in 100 cc of hexane. The solution is placed in a 250 cc. flask equipped with a sparger supplied by an air source, a stirrer, and a heater. Air is bubbled in at room temperature at a rate of 20 ml./minute during 20 hours. Solvent is replaced as required in order to maintain the original volume of solution. At the end of the reaction period the solvent is flash-evaporated and the resulting mixture is purified by column chromatography to yield 3 g. of bis(2-methyl-3-furyl)disulfide.

The purified bis(2-methyl-3-furyl) disulfide has a full meat flavor and a cooked meat aroma when used in soup base at a concentration of 0.2 p.p.m. In a comparison 5-methyl-2-furyl disulfide is also used in soup base at a concentration of 0.2 ppm and is found to have only a chemical, rubbery taste and aroma.

The analytical data for the 3-furyl disulfide follows:

| | Infra-red |
|---|---|
| $\lambda_{max.}$ | Interpretation |
| 3.22 | Aromatic C—H stretch. |
| 6.32, 6.60 | Aromatic C=C stretch. |
| 7.22 | Methyl group. |
| 11.28 | Furanic ring vibration. |
| 13.6 | C—H out-of-plane blend of a 2,3-disubstituted furan. |

Proton magnetic resonance
In carbon tetrachloride:
7.14 (doublet, 2 protons),
6.25 (doublet, 2 protons), and
2.07 ppm (singlet, 6 protons).

Mass spectrum

Base peak 113; molecular peak, 226; other peaks in descending order: 43, 45, 51, 114, 85.

EXAMPLE III

The following ingredients are homogeneously admixed at 25° C.:

| Ingredient | Amount (g.) |
|---|---|
| 2-methylfuran-3-thiol | 2.0 |
| 2-methyl-[4,5H]-dihydrofuran-3-thiol | 0.5 |
| Bis(2-methyl-3-furyl)disulfide | 93.0 |
| Bis(2-methyl-3-furyl) monosulfide | 4.0 |
| Bis(2-methyl-3-furyl)trisulfide | 0.5 |

The mixture has an excellent roasted-meat flavor when used in a soup base at 10 ppm.

EXAMPLE IV

The following ingredients are selected and mixed as described in Example III to yield compositions having excellent meat flavor:

| Mixture A | |
|---|---|
| Ingredient: | Amount (Parts/100 Total) |
| 2-methylfuran-3-thiol | 5 |
| 2-methyl-3-thio-[4,5H]-dihydrofuran | 5 |
| Bis(2-methyl-3-furyl) disulfide | 1 |
| Bis(2-methyl-3-furyl) monosulfide | 89 |
| Mixture B | |
| 2-ethylfuran-3-thiol | 9 |
| 2-butylfuran-3-thiol | 9 |
| Bis(2-pentyl-3-furyl) trisulfide | 30 |
| Bis(2-ethyl-5-isopropyl-[2,3H]-dihydro-3-furyl) trisulfide | 1 |
| Bis(2-butyltetrahydro-3-furyl)monosulfide | 1 |
| Gum arabic | 50 |

EXAMPLE V

Preparation of 2-methyl-3-furanthiol

A 500 cc. three-neck round-bottom flask is fitted with a Y-tube, thermometer, and stirrer and is then charged with 32 g. of fuming sulfuric acid (oleum) containing 20% $SO_3$. The temperature is maintained at 24°–28° C., and 40 g. (0.318 mol) of 5-methyl-2-furoic acid is slowly added to the oleum during a period of 45 minutes. After addition is complete, the reaction mixture is stirred for an additional 2¼ hours and then held for 16 hours.

The reaction mixture is thereupon poured over 600 cc. of ice-water mixture and neutralized to pH 5 with 430 g. barium carbonate, during which neutralization a thick paste forms. After addition of 500 cc. of water, the paste is boiled and then vacuum-filtered while hot. The barium sulfate-containing solids which remain after filtration are boiled with 700 cc. of water, and the mixture is vacuum-filtered while hot. Both filtrates are combined and refrigerated for 2 days to form crystals which are recovered. The filtrate is evaporated to a volume of about 500 cc. and cooled in ice to recover further crystals. The remaining filtrate is evaporated to a volume of 50 cc., 100 cc. of methanol is added, and the liquid is chilled to obtain crystals. The yield of solids (barium-2-methyl-3-sulfo-5-furoic acid) from the three crystallizations is 93.5 g.

Barium-2-methyl-3-sulfo-5-furoic acid in the amount of 98.2 g. and 1800 cc. of distilled water is charged to a flask, and the flask is heated in a steam bath to 70° C. until all the solids are dissolved. Then, 116 g. of 20% aqueous sulfuric acid is gradually added to precipitate barium sulfate. The decanted liquid is cooled in ice and filtered. The water is evaporated from the filtrate, and the remainder is evaporated under high vacuum at room temperature to obtain 35.1 g. of yellow oil which crystallizes after being held in a desiccator overnight.

The sodium salt of the sulfo furoic acid is prepared by dissolving 33.1 g. of the crystallized oil (sulfo furoic acid) in 100 cc. of water and gradually adding 6.75 g. of sodium bicarbonate. After drying in a steam bath and then in a vacuum desiccator, 37.4 g. of the sodium salt containing water of crystallization is obtained.

The sodium salt is decarboxylated by charging 13.2 g. of mercuric chloride ($HgCl_2$) in 60 cc. of water to a 500 cc. three-neck round-bottom flask fitted with a condenser having a gas outlet and with a Y-tube, a nitrogen inlet, a stirrer, and a heating mantle. Then 11.1 g. of the sulfo furoic acid sodium salt in 80 cc. of water is charged to the flask, and this is followed by 1.95 g. of sodium hydroxide in 20 cc. of water. The mixture is refluxed for 2 hours and 40 minutes while the pH is maintained at 4–5 by addition of aqueous sodium hydroxide or hydrochloric acid as required, and carbon dioxide evolves. The mixture is then cooled to room temperature and filtered. The filtrate is adjusted to pH 7–8 with 10% aqueous sodium bicarbonate, and hydrogen sulfide is bubbled through the mixture to precipitate mercuric sulfide. The mercuric sulfide is separated by filtration and the filtrate is concentrated in a rotary evaporator. About 30 cc. of water is added to dissolve all the solids after concentration and the mixture is cooled to crystallize out 4.93 g. of 2-methylfuran-3-sulfonic material. The crystals are filtered from the supernatant and dried.

The sulfonic acid derivative is converted to the sulfonyl chloride derivative by treatment of 1.3 g of the sulfonic acid with 33 g. of thionyl chloride and two drops of dimethyl formamide for 75 minutes at 25° C. The excess thionyl chloride is removed on a rotary evaporator, the residue is washed with benzene, and the benzene is stripped off to obtain 0.88 g. of amber oil having a sharp, meaty odor.

The amber oil so obtained is then reacted with 0.8 g. of lithium aluminum hydride in 30 cc. of diethyl ether. The reaction is carried out by adding the hydride to 20 cc. of ether, filtering, adding the oil in 10 cc. of ether at reflux during a period of 8 minutes. The reflux is then continued for 75 minutes. After reflux the remaining hydride in the mixture is reacted with methanol in ether, and the product so obtained is poured into ice water, acidified to pH 1 with hydrochloric acid, and extracted with ether to obtain an oil. This oil is dried, filtered, and stripped of ether to obtain 0.27 g. of a yellow oil having a good meaty aroma.

Proton magnetic resonance of the major peak obtained from this oil by gas-liquid chromatography shows a thiol. Mass spectroscopy of this material shows peak at 114 and 113. These results confirm the production of the 2-methyl-3-furanthiol.

EXAMPLE IV

Isolation of bis(furyl) disulfides from a reaction mixture

A 4,000-pound batch having the following composition:

| | Parts |
|---|---|
| Thiamine hydrochloride | 8.8 |
| L-cysteine hydrochloride | 8.8 |
| Maggi 4 BE protein hydrolysate | 309.6 |
| Water | 672.8 |
| | 1,000.0 | is heated at reflux for four hours. After the first 45 minutes of reflux a total off 40 gallons condensate is removed uniformly over the next 3 hours and 15 minutes. Each gallon of condensate is extracted with 400 ml. portions of methylene chloride. After removal of the methylene chloride under very mild vacuum, a 50 ml. residue is obtained which possesses an extremely powerful roastmeat aroma.

Preparative thin-layer chromatography (8 × 8″ × 1.25 mm., silica-gel G, 200 >/plate) of approximately 2.4 g. gave 0.066 g. of a pure compound having a good basic roast-meat aroma upon proper dilution. The mass spectrum of this compound is as follows: m/e (rel. intensity) 226 (9.6), 227 (1.9), 228 (1.7), 113 (10.0), 43 (4.7), 114 (4.4), 45 (3.6), 85 (3.1), 51 (2.9), 69 (17.6). Proton magnetic resonance in carbon tetrachloride shows 2.07

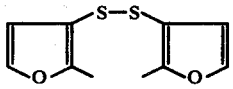

6.25 (doublet, 2 furyl protons), and 7.14 p.p.m. (doublet, 2 furyl protons).

The above data are in excellent agreement with the proposed structure of bis(2-methyl-3-furyl) disulfide:

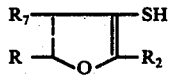

When the crude extract is analyzed by preparative gas/liquid chromatography a compound having a very intense pot roast odor is obtained. This compound has been identified as 2-methyl-furan-3-thiol.

What is claimed is:

1. A furanthiol having the formula

wherein $R_2$ is alkyl containing 2 to 5 carbon atoms, each of $R_3$ and $R_7$ is hydrogen or alkyl containing 1 to 5 carbon atoms and the dashed line represents a single or double carbon-to-carbon bond.

2. Substantially pure 2-methylfuran-3-thiol having a λmax at 3.92, 6.60, 7.26, 7.40, and 13.58μ by infrared spectroscopy.

3. A dihydrofuranthiol having the formula

wherein $R_2$ is alkyl containing 1 to 5 carbon atoms, and each of $R_3$ and $R_7$ is hydrogen or alkyl containing 1 to 5 carbon atoms.

4. A dihydrofuranthiol as defined in claim 3 wherein $R_7$ is hydrogen, and $R_2$ and $R_3$ is hydrogen or methyl.

5. A dihydrofuranthiol as defined in claim 3 wherein $R_7$ is hydrogen, $R_2$ is methyl, and $R_3$ is hydrogen or methyl.

6. 2-Methyl-[4,5H]-dihydrofuran-3-thiol.

7. 2,5-Dimethyl-[4,5H]-dihydrofuran-3-thiol.

8. 2,5-Dimethyltetrahydrofuran-3-thiol.

9. A substantially pure form of a furanthiol of the formula:

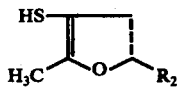

wherein $R_2$ is hydrogen or methyl and the dashed line represents a single or double carbon-to-carbon bond.

10. A substantially pure form of the compound of the formula

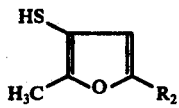

wherein $R_2$ is hydrogen or methyl.

* * * * *

UNITED STATES PATENT AND TRADEMARK OFFICE
CERTIFICATE OF CORRECTION

PATENT NO. : 4,055,578
DATED : October 25, 1977
INVENTOR(S) : WILLIAM JOHN EVERS It is certified that error appears in the above-identified patent and that said Letters Patent are hereby corrected as shown below:

Col. 10, line 43, "EXAMPLE IV" should read --EXAMPLE VI--

Signed and Sealed this

Thirtieth Day of May 1978

[SEAL]

Attest:

RUTH C. MASON
Attesting Officer

LUTRELLE F. PARKER
Acting Commissioner of Patents and Trademarks